United States Patent [19]

Olsen

[11] 4,027,529
[45] June 7, 1977

[54] METHOD AND APPARATUS FOR TESTING SPOT WELDS

[76] Inventor: Robert A. Olsen, 140 Hartman Circle NE., Fridley, Minn. 55432

[22] Filed: Mar. 24, 1976

[21] Appl. No.: 669,829

[52] U.S. Cl. .................................. 73/88 B; 73/103
[51] Int. Cl.² ......................................... G01N 3/00
[58] Field of Search ................ 73/88 B, 88 R, 88 F, 73/103, 100, 96; 29/278

[56] References Cited

UNITED STATES PATENTS

| | | | |
|---|---|---|---|
| 1,678,017 | 7/1928 | Midgley | 73/100 |
| 2,377,869 | 6/1945 | Elliott | 73/88 B |
| 3,636,758 | 1/1972 | McKee et al. | 73/100 |

Primary Examiner—James J. Gill
Assistant Examiner—Anthony V. Ciarlante
Attorney, Agent, or Firm—John W. Adams

[57] ABSTRACT

A method and apparatus for testing the integrity of spot welds made by a welding machine without destroying the manufactured parts being produced, said method and apparatus including welding together a pair of angle members made from the same sheet material as the parts being manufactured to form a "T-shaped" test specimen with the outwardly extending cross arm of this "T" forming attachment portions and providing a testing tool constructed and arranged to pull apart the welded together portions of the angles and test the integrity of the weld with a minimum of force being applied thereto.

3 Claims, 5 Drawing Figures

U.S. Patent
June 7, 1977
4,027,529
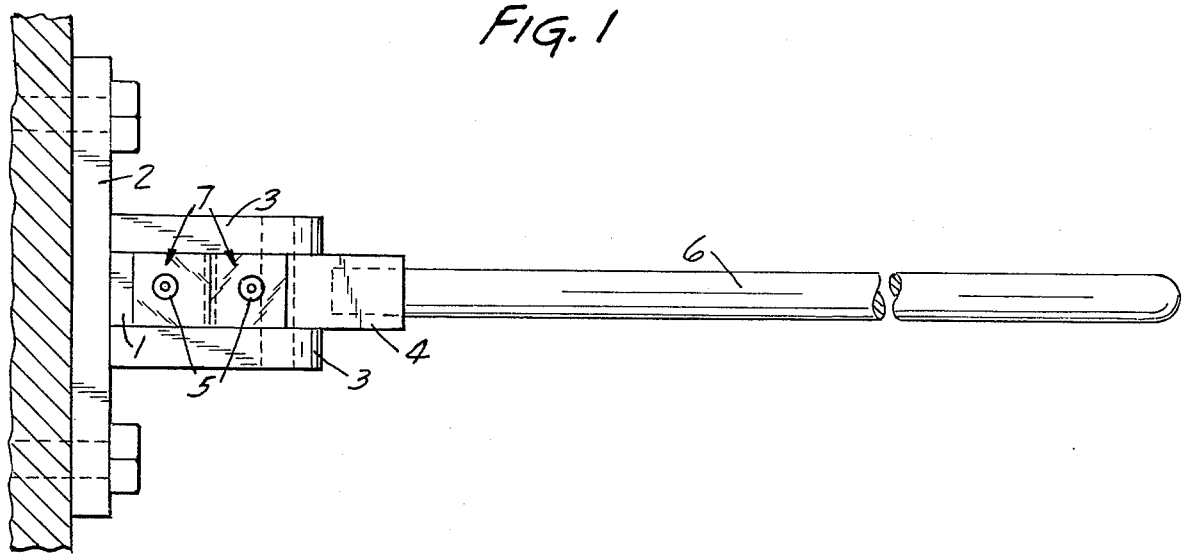
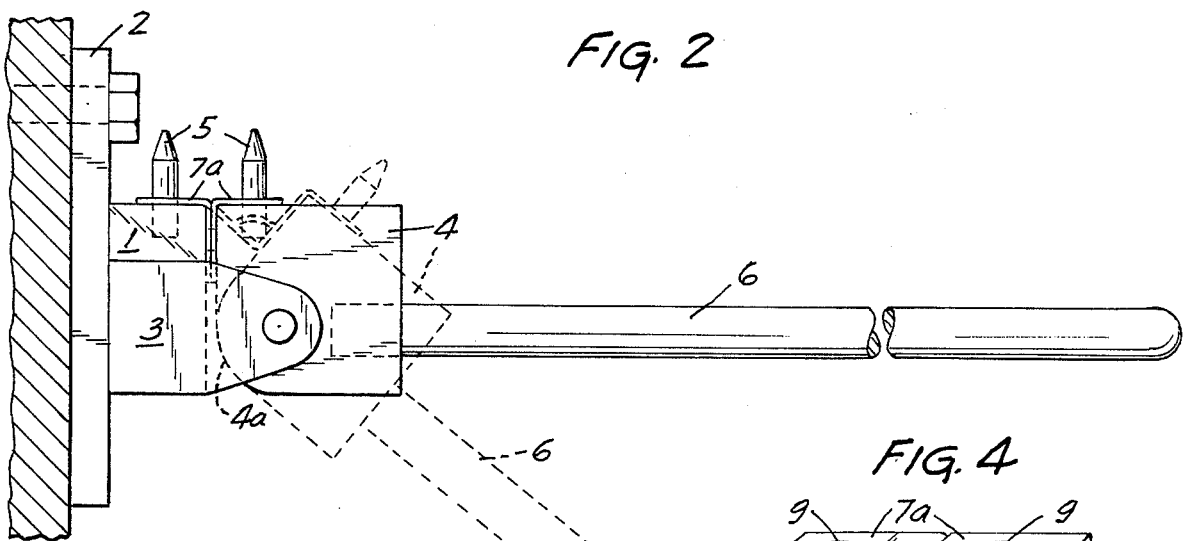
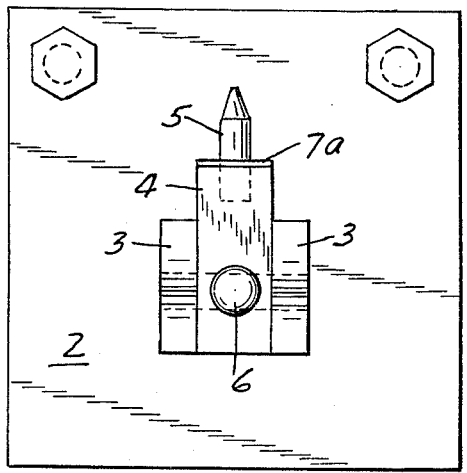
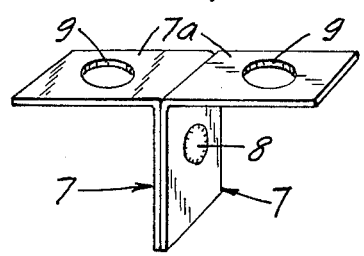
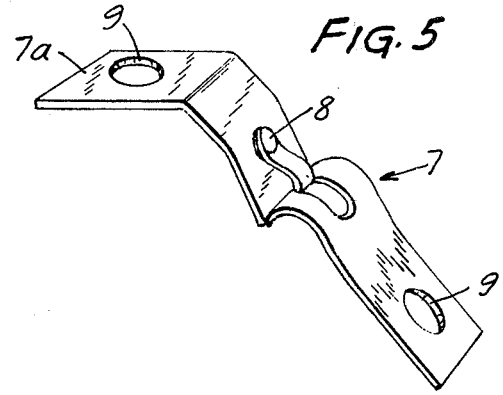

METHOD AND APPARATUS FOR TESTING SPOT WELDS

Present test procedures for testing the integrity of welded parts require the destruction of the part to actually test the weld. This is, of course, expensive and impractical since it destroys the welded parts. With my method and apparatus test samples or specimens are produced for conducting the destruction test of the weld integrity. The specimens are constructed from materials substantially identical to the materials from which the production parts are being manufactured, and in the present invention T-shaped test specimens are constructed in the form of a pair of angle elements having one leg of each element spot welded to leg of the other angle in face to face relation thereto to form the web of the "T" and with the other legs extending outwardly in substantial alignment with each other and away from the welded together legs to form the cross portion of the "T". The outwardly extending legs provide attachment portions which are adapted to be quickly and easily attached to a testing tool designed to produce a peeling-apart force on the welded together legs. If the integrity of the weld is satisfactory, a sufficient size "nugget" will be pulled out of the material surrounding the weld of one of the welded together legs, indicating that the spot welding machine is operating properly and produce satisfactory production parts. The setting of the spot welding machine is, of course, critical in producing satisfactory welded parts and if the welds on the test specimens are of acceptable quality it can be assumed that the welds of the production parts being made will also be of acceptable quality. This peeling action produces a satisfactory test with a minimum of force being required.

It is an object of the present invention to provide an apparatus for testing the integrity of a spot weld produced by a welding machine by constructing a test specimen comprising a pair of angle elements, one leg of one element being spot welded in face to face relation with one leg of the other element, the unwelded legs of the two angles extending outwardly in aligned relation with each other to form the T-shaped test specimen, the unwelded legs being adapted to be attached to a tool for pulling the same apart and peeling the welded together portions apart and thereby determine the integrity of said weld.

It is a further object of the present invention to provide attachment means to quickly and easily attach said specimen to said tool.

It is another object of the present invention to provide a method of testing the integrity of a spot weld produced by a welding machine by welding together two legs of a pair of angle elements to form a T-shaped test specimen with the unwelded legs extending outwardly in substantial aligned relation to each other to form attachment portions and attaching said attachment portions to a test tool which exerts sufficient peeling force upon said welded together legs to determine the integrity of said weld.

The objects of the invention will more fully appear from the following description made in connection with the drawings in which:

FIG. 1 is a top plan view of the test tool and a test specimen attached thereto;

FIG. 2 is a side elevational view of the test tool and attached specimen and showing by broken lines the peeling action produced by said tool;

FIG. 3 is a front elevational view of said tool and attached specimen;

FIG. 4 is a perspective view of a test specimen; and

FIG. 5 is a perspective view of a test specimen peeled apart by said test tool.

Referring now to the drawings, a fixed peeling member 1 is attached to a base 2. The base 2 is mounted in fixed relation on a wall or other support at a convenient location near the welding machine (not shown). A pair of pivot support ears 3 are fixed to opposite sides of fixed peeling member 1 and extend outwardly beyond the front face thereof, as best shown in FIG. 2. A pivoted peeling member 4 is mounted on a pivot pin carried by the ears 3 and has a top surface horizontally aligned with the top surface of fixed peeling member 1 when the pivoted member 4, is in its initial closed position. A pair of attachment elements, or posts, 5 are respectively fixed to the upper faces of members 1 and 4 and are spaced apart a predetermined distance when the upper faces of members 1 and 4 are in aligned coplanar relationship. An actuating lever 6 is attached to the front of pivoted peeling member 4.

A T-shaped test specimen is shown in perspective in FIG. 4, and is formed from a pair of angle elements 7. One leg of one angle 7 is connected by a spot weld 8 in face to face relation to one leg of the other angle to form the depending web of the T-shaped specimen and define a weld plane therebetween. The unwelded legs of the angles 7 extend outwardly in generally aligned coplanar relation generally normal to the welded together legs to provide attachment elements or legs 7a and form the cross portion of the T-shaped specimen. A hole 9 is formed in each attachment element 7a said holes 9 being spaced apart the same distance as the posts 5 when members 1 and 4 are in initial closed position.

The angle elements 7 are of the same sheet metal material as the welded products being manufactured and are spot welded together to form the T-shaped test specimen shown in FIG. 4. The holes 9 of the specimen are fitted over the posts 5 and in the form shown with the welded together legs forming the web of the "T" inserted between peeling members 1 and 4. Pivoted member 4 is then pivoted away from stationary peeling member 1 by pulling downwardly on handle 6, the corner 4a of member 4 being of arcuate shape to permit free pivoting of member 4. As member 4 is so pivoted, sufficient peeling force is exerted upon the welded together legs of test specimen 7 to separate the same and if the weld is sound, a "nugget" which is substantially equal to the diameter of the weld 8 will be torn out or peeled away from said weld as shown in FIG. 5, indicating that the weld is satisfactory. If the weld does not hold but breaks and the welded together legs separate without tearing out the material of one of the legs of the test specimen, or even if a nugget smaller than the diameter of the weld is produced, this indicates that the spot welding machine is not properly adjusted for the type of material being welded and the machine is readjusted and the procedure repeated until satisfactory welds are produced.

The method embodied in this invention consists in welding together one leg each of a pair of angle elements in face to face relation with the unwelded legs extending outwardly in substantially aligned coplanar relation from the welded together legs to form attachment portions for a generally T-shaped test specimen. Outwardly directed tensioning force is applied to said attachment portions 7a by the members 1 and 4 to peel apart the welded together legs.

It will be course be understood that various changes may be made in the form, details, arrangement and proportions of the parts without departing from the scope of this invention as set forth in the appended claims.

What is claimed is:

1. Apparatus for testing the integrity of a spot weld produced by a welding machine without destruction of the manufactured sheet metal parts, said apparatus comprising a test specimen made from a pair of angle elements constructed from the same sheet material as the manufactured products being welded, said elements having connected leg portions welded together by the production welding machine in face to face relation to define a weld plane therebetween, the other legs of said angles extending oppositely outwardly normal to said plane to form a T-shaped specimen and provide a pair of coplanar attachment portions, a testing tool having a pair of pivoted peeling members constructed and arranged for respective attachment to said attachment portions of said test specimen and including means for forceably pivoting said peeling members to peel apart the connected leg portions and determine the integrity of the weld.

2. The structure set forth in claim 1 wherein said test specimen is provided with a pair of attachment holes respectively formed in said attachment portions, said peeling members having aligned coplanar top faces when in initial closed position, a pair of upstanding attachment posts respectively fixed in upstanding relation to said top faces and spaced apart the same distance as the holes in said specimen when said peeling members are in closed position to permit said posts to be received through said holes for attachment of the test specimen to said peeling members with the welded together portions of said specimen being disposed between said peeling members so that pivoting force exerted on said peeling members produces a peeling action of said welded together specimen portions.

3. The method for testing the integrity of a spot weld produced by a welding without destruction of the manufactured sheet metal parts, said method comprising producing a T-shaped test specimen having a depending web portion and a cross portion of the "T" by spot welding together a pair of angle elements constructed from the same sheet material as the manufactured parts being produced to provide a pair of laterally extending attachment portions forming the cross of the "T" and the welded together portions forming the depending web thereof, applying pivotally directed tension to the attachment portions to peel apart the depending welded together portions and thus determine the integrity of the weld therebetween.

* * * * *